(12) United States Patent
Chen et al.

(10) Patent No.: US 11,583,313 B1
(45) Date of Patent: Feb. 21, 2023

(54) SURGICAL ACCESS SHEATH AND METHODS OF USE

(71) Applicant: SPIWay LLC, Carlsbad, CA (US)

(72) Inventors: Eugene Chen, Carlsbad, CA (US); Richard C. Ewers, Carlsbad, CA (US); Cang Lam, Irvine, CA (US); Stephanie Frimond, Carlsbad, CA (US)

(73) Assignee: SPIWAY LLC, Carlsbad, CA (US)

( * ) Notice: Subject to any disclaimer, the term of this patent is extended or adjusted under 35 U.S.C. 154(b) by 250 days.

(21) Appl. No.: 16/696,741

(22) Filed: Nov. 26, 2019

Related U.S. Application Data

(60) Provisional application No. 62/776,111, filed on Dec. 6, 2018.

(51) Int. Cl.
  *A61B 17/34* (2006.01)
  *A61B 17/24* (2006.01)
  *A61B 17/3201* (2006.01)

(52) U.S. Cl.
  CPC .......... *A61B 17/3423* (2013.01); *A61B 17/24* (2013.01); *A61B 17/3201* (2013.01); *A61B 2017/3429* (2013.01)

(58) Field of Classification Search
  CPC ... A61F 2/04; A61F 2/95; A61F 2/958; A61B 2017/1205; A61B 2017/0409; A61B 2017/0414
  See application file for complete search history.

(56) References Cited

U.S. PATENT DOCUMENTS

| | | |
|---|---|---|
| 2,335,936 A | 12/1943 | Hanlon |
| 3,568,678 A | 3/1971 | Pourquier et al. |
| 3,664,330 A | 5/1972 | Deutsch |
| 3,867,946 A | 2/1975 | Huddy |
| 4,280,493 A | 7/1981 | Council |
| 4,312,353 A | 1/1982 | Shahbabian |
| 4,755,174 A | 7/1988 | Milewski et al. |
| 4,819,619 A | 4/1989 | Augustine et al. |
| 4,821,715 A | 4/1989 | Downing |

(Continued)

FOREIGN PATENT DOCUMENTS

| | | |
|---|---|---|
| CA | 2185070 C | 3/1997 |
| DE | 1057738 B | 5/1959 |

(Continued)

OTHER PUBLICATIONS

WIPO, International Search Report and Written Opinion for International Application No. PCT/US2017/047550, dated Nov. 30, 2017. 14 pages.

*Primary Examiner* — Vi X Nguyen
(74) *Attorney, Agent, or Firm* — Perkins Coie LLP

(57) ABSTRACT

In a surgical method, an access sheath is provided by a tube of a braided material. A first end of the sheath may be folded. The first end, folded or unfolded, is grasped with a distal end of a tool, which is then inserted into the nose of a patient. Advancing the tool pulls the distal end of the sheath into the nose of the patient. The sheath is then released from the tool and the tool is withdrawn. A portion of the sheath may be optionally cut off to shorten the sheath to a desired length. Typically the sheath has a total length of 70 to 180 mm and an outside diameter of 12 to 50 mm. The sheath may have a constant outside diameter along its length. The sheath may comprise silicone on the braided material.

15 Claims, 4 Drawing Sheets

(56) References Cited

U.S. PATENT DOCUMENTS

| | | |
|---|---|---|
| 4,883,465 A | 11/1989 | Brennan |
| 5,011,474 A | 4/1991 | Brennan |
| 5,139,510 A | 8/1992 | Goldsmith, III et al. |
| 5,336,163 A | 8/1994 | DeMane et al. |
| 5,400,770 A | 3/1995 | Nakao et al. |
| 5,591,226 A | 1/1997 | Trerotola et al. |
| 5,599,284 A | 2/1997 | Shea |
| 5,601,591 A | 2/1997 | Edwards et al. |
| 5,601,594 A | 2/1997 | Best |
| 5,609,627 A | 3/1997 | Goicoechea et al. |
| 5,709,713 A | 1/1998 | Evans et al. |
| 5,713,839 A | 2/1998 | Shea |
| 5,800,394 A | 9/1998 | Yoon et al. |
| 5,827,224 A | 10/1998 | Shipped |
| 5,865,728 A | 2/1999 | Moll et al. |
| 5,876,445 A | 3/1999 | Andersen et al. |
| 5,967,970 A | 10/1999 | Cowan et al. |
| 5,993,407 A | 11/1999 | Moazed |
| 6,033,426 A | 3/2000 | Kaji |
| 6,083,155 A | 7/2000 | Trese |
| 6,102,928 A | 8/2000 | Bonutti |
| 6,183,493 B1 | 2/2001 | Zammit |
| 6,186,965 B1 | 2/2001 | Patterson |
| 6,306,084 B1 | 10/2001 | Pinczower |
| 6,309,345 B1 | 10/2001 | Stelzer et al. |
| 6,328,753 B1 | 12/2001 | Zammit |
| 6,386,197 B1 | 5/2002 | Miller |
| 6,454,783 B1 | 9/2002 | Piskun |
| 6,468,301 B1 | 10/2002 | Amplatz et al. |
| 6,491,720 B1 | 12/2002 | Vallana et al. |
| 6,607,546 B1 | 8/2003 | Murken |
| 7,100,612 B2 | 9/2006 | Dunlap |
| 7,361,168 B2 | 4/2008 | Makower et al. |
| 7,410,480 B2 | 8/2008 | Muni et al. |
| 7,520,876 B2 | 4/2009 | Ressemann et al. |
| 7,654,997 B2 | 2/2010 | Makower et al. |
| 7,678,099 B2 | 3/2010 | Ressemann et al. |
| 7,720,521 B2 | 5/2010 | Chang et al. |
| 7,727,186 B2 | 6/2010 | Makower et al. |
| 7,730,888 B2 | 6/2010 | Dunlap |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,799,337 B2 | 9/2010 | Levin |
| 7,918,871 B2 | 4/2011 | Truitt et al. |
| 8,409,083 B2 | 4/2013 | Mangiardi |
| 8,839,790 B2 | 9/2014 | Beck |
| 8,986,201 B2 | 3/2015 | Chen et al. |
| 9,011,326 B2 | 4/2015 | Hannaford et al. |
| 10,675,114 B2 | 6/2020 | Ewers et al. |
| 2001/0049551 A1 | 12/2001 | Tseng et al. |
| 2002/0013511 A1 | 1/2002 | Ailinger et al. |
| 2003/0014076 A1 | 1/2003 | Mollenauer et al. |
| 2003/0154986 A1 | 8/2003 | Fariss et al. |
| 2003/0216770 A1 | 11/2003 | Persidsky et al. |
| 2004/0116999 A1 | 6/2004 | Ledergerber |
| 2004/0138525 A1 | 7/2004 | Saadat et al. |
| 2004/0210114 A1 | 10/2004 | Simon |
| 2004/0230100 A1 | 11/2004 | Shluzas |
| 2004/0243172 A1 | 12/2004 | Hogle |
| 2005/0059960 A1 | 3/2005 | Simaan et al. |
| 2005/0075540 A1 | 4/2005 | Shluzas et al. |
| 2005/0090717 A1 | 4/2005 | Bonadio et al. |
| 2005/0165366 A1 | 7/2005 | Brustad et al. |
| 2005/0192608 A1 | 9/2005 | Moreno et al. |
| 2005/0240147 A1 | 10/2005 | Makower et al. |
| 2006/0004323 A1 | 1/2006 | Chang et al. |
| 2006/0041270 A1 | 2/2006 | Lenker et al. |
| 2006/0095050 A1 | 5/2006 | Hartley et al. |
| 2006/0173407 A1 | 8/2006 | Shaughnessy et al. |
| 2006/0200003 A1 | 9/2006 | Youssef |
| 2006/0212062 A1 | 9/2006 | Farascioni |
| 2006/0287583 A1 | 12/2006 | Mangiardi |
| 2007/0005094 A1 | 1/2007 | Eaton et al. |
| 2007/0016174 A1 | 1/2007 | Millman et al. |
| 2007/0021773 A1 | 1/2007 | Nolte |
| 2007/0055107 A1 | 3/2007 | Wenchell |
| 2007/0100370 A1 | 5/2007 | Hogle |
| 2007/0191876 A1 | 8/2007 | Dubrul et al. |
| 2007/0203474 A1 | 8/2007 | Ryan et al. |
| 2007/0219575 A1 | 9/2007 | Mejia |
| 2007/0225568 A1 | 9/2007 | Colleran |
| 2007/0277831 A1 | 12/2007 | Luhrs |
| 2007/0293726 A1 | 12/2007 | Goldfarb et al. |
| 2007/0299314 A1 | 12/2007 | Bertolero et al. |
| 2008/0027464 A1 | 1/2008 | Moll et al. |
| 2008/0045803 A1 | 2/2008 | Williams et al. |
| 2008/0058590 A1 | 3/2008 | Saadat et al. |
| 2008/0065105 A1 | 3/2008 | Larkin et al. |
| 2008/0065108 A1 | 3/2008 | Diolaiti |
| 2008/0071288 A1 | 3/2008 | Larkin et al. |
| 2008/0097514 A1 | 4/2008 | Chang et al. |
| 2008/0097516 A1 | 4/2008 | Chang et al. |
| 2008/0109026 A1 | 5/2008 | Kassam |
| 2008/0132938 A1 | 6/2008 | Chang et al. |
| 2008/0188868 A1 | 8/2008 | Weitzner et al. |
| 2008/0234550 A1 | 9/2008 | Hawkes et al. |
| 2008/0243064 A1 | 10/2008 | Stabler et al. |
| 2008/0255519 A1 | 10/2008 | Piskun et al. |
| 2008/0275483 A1 | 11/2008 | Makower et al. |
| 2009/0010991 A1 | 1/2009 | Prabhu et al. |
| 2009/0054728 A1 | 2/2009 | Trusty |
| 2009/0062927 A1 | 3/2009 | Marten et al. |
| 2009/0137952 A1 | 5/2009 | Ramamurthy et al. |
| 2009/0250067 A1 | 10/2009 | Arnon |
| 2009/0312745 A1 | 12/2009 | Goldfarb et al. |
| 2010/0030031 A1 | 2/2010 | Goldfarb et al. |
| 2010/0076555 A1 | 3/2010 | Marten et al. |
| 2010/0100181 A1 | 4/2010 | Makower et al. |
| 2010/0145147 A1 | 6/2010 | Pinsky et al. |
| 2010/0174149 A1 | 7/2010 | Moll et al. |
| 2010/0174308 A1 | 7/2010 | Chang et al. |
| 2010/0179537 A1 | 7/2010 | Rashidi |
| 2010/0211181 A1 | 8/2010 | Prabhu et al. |
| 2010/0228227 A1 | 9/2010 | Krespi et al. |
| 2010/0249523 A1 | 9/2010 | Spiegal et al. |
| 2010/0298862 A1 | 11/2010 | Chang et al. |
| 2010/0331777 A1 | 12/2010 | Danielsson |
| 2011/0004194 A1 | 1/2011 | Eaton et al. |
| 2011/0048430 A1 | 3/2011 | Arnon |
| 2011/0118551 A1* | 5/2011 | Ciporen ............... A61B 90/00 600/201 |
| 2011/0125092 A1 | 5/2011 | Hepworth et al. |
| 2011/0172495 A1 | 7/2011 | Armstrong |
| 2012/0203069 A1 | 8/2012 | Hannaford et al. |
| 2013/0092173 A1 | 4/2013 | Alexander et al. |
| 2013/0190571 A1 | 7/2013 | Chen et al. |
| 2014/0024994 A1 | 1/2014 | Khoury et al. |
| 2015/0209074 A1 | 7/2015 | Payne |
| 2016/0249934 A1 | 9/2016 | Hewitt et al. |
| 2017/0347865 A1* | 12/2017 | Chen ..................... A61B 17/29 |
| 2018/0256146 A1 | 9/2018 | Chen et al. |
| 2018/0303631 A1 | 10/2018 | Phan et al. |
| 2018/0361129 A1 | 12/2018 | Renner et al. |
| 2019/0104929 A1 | 4/2019 | Chen et al. |

FOREIGN PATENT DOCUMENTS

| | | |
|---|---|---|
| DE | 1222209 B | 8/1966 |
| DE | 202012100028 U1 | 4/2012 |
| DE | 102010054786 A1 | 6/2012 |
| DE | 202010017673 U1 | 10/2012 |
| EM | 002429829-0001 | 3/2014 |
| EP | 1785165 A1 | 5/2007 |
| FR | 2260979 A1 | 9/1975 |
| FR | 2825281 A1 | 12/2002 |
| FR | 2985660 A1 | 7/2013 |
| WO | 2010107894 A1 | 9/2010 |
| WO | 2011013122 A2 | 2/2011 |
| WO | 2011013122 A3 | 4/2011 |
| WO | 2015198032 A1 | 12/2015 |

* cited by examiner

SURGICAL ACCESS SHEATH AND METHODS OF USE

CROSS-REFERENCE TO RELATED APPLICATION(S)

This application claims priority to U.S. Provisional Application No. 62/776,111 filed Dec. 6, 2018 and incorporated herein by reference.

BACKGROUND

Endoscopic surgery within the head is a common procedure in neurological surgery and otolaryngology. It avoids large cranial incisions and can reduce the need for brain retraction and prolonged wound healing. Endoscopic surgery within the head also provides improved illumination and visualization of the target tissues because the camera of the endoscope is brought directly to the surgical site.

During this type of surgery, there may be local trauma to the tissues in the surgical pathway, resulting from pressure or abrasion caused by the surgical tools. Generally these tissues are the nasal mucosa, turbinates, nasal septum, and sphenoid/frontal/maxillary sinus. Surgical pathway trauma can add to the trauma of the procedure and prolong the patient's recovery time. Liquids in the surgical pathway, such as mucous, blood, and soiled irrigation fluid, tend to obscure the view of the endoscope. This leads to the constant need for irrigation and suction of the obstructing liquids. In some cases the endoscope may also have to be removed, cleaned and replaced multiple times during a single procedure. This disadvantage tends to increase the complexity and time requirements of the operation. In addition, with each movement of a surgical tool into or out of the surgical pathway, the surrounding tissues are put at risk of additional trauma. Improved devices and methods are therefore needed.

SUMMARY

An access sheath is provided to protect the nasal passageway during endoscopic trans nasal or intra ocular surgery. The access sheath protects the entrance of the nares and sinus from the placement and manipulation of surgical tools both during the initial placement and during manipulation and exchange of surgical tools. The access sheath may provide a guide port to help direct surgical tools into position.

In a surgical method, an access sheath is provided by a tube of a braided material. A first end of the sheath may be folded. The first end, folded or unfolded, is grasped with a distal end of a tool, which is then inserted into the nose of a patient. Advancing the tool pulls the distal end of the sheath into the nose of the patient. The sheath is then released from the tool and the tool is withdrawn. A portion of the sheath may optionally be cut off to shorten the sheath to a desired length. Typically the sheath has a total length of 60 to 180 mm and an outside diameter of 12 to 40 or 50 mm. The sheath may have a constant outside diameter along its length. The sheath may have a layer of silicone on the braided material.

DETAILED DESCRIPTION

Figure 1:
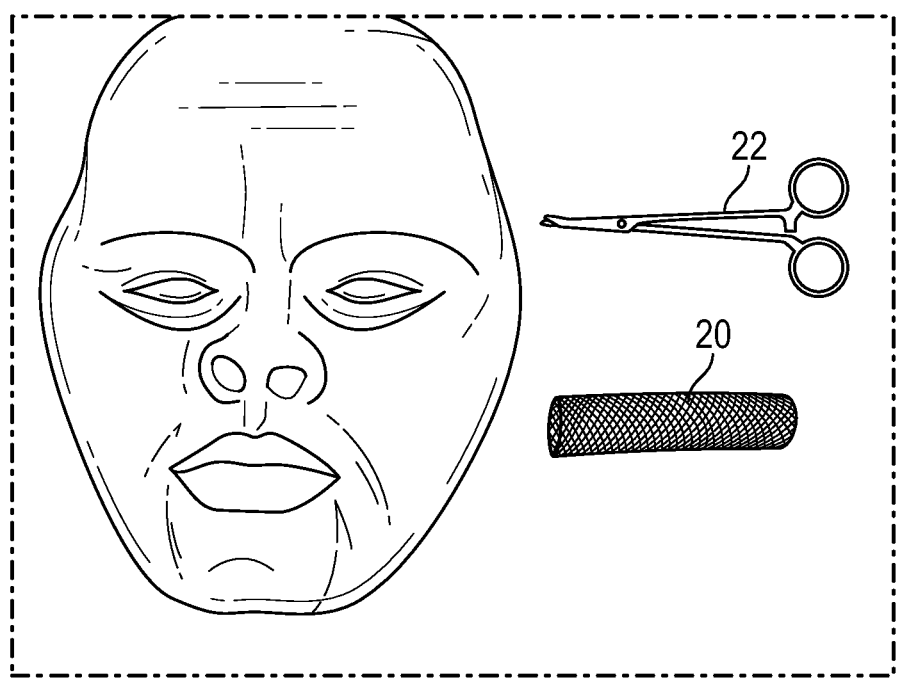
FIG. 1 is a front perspective view of a tubular braided access sheath and a deployment tool alongside a human head model.

As shown in FIG. 1, an access sheath 20 may be provided as a length of tubular braided material. Generally, the sheath is flexible and can conform to varying anatomies. The sheath 20, for example in the form of a braided tube, requires no special features or shaping. The distal end of the braided tube 20 may optionally be sealed, folded, bonded, etc., to prevent fraying. The braided tube may advantageously have a coating of a sealing material such as silicone, for example as described in U.S. Patent Application Publication No. 2019/0104929, incorporated herein by reference.

Figure 2:
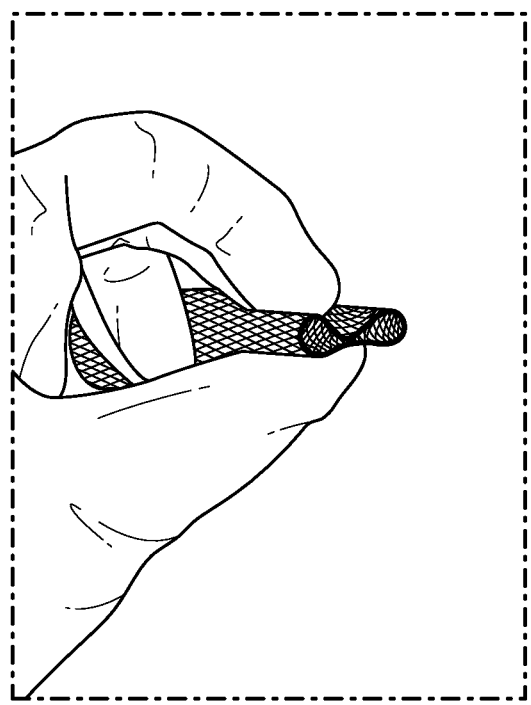
FIG. 2 is a perspective view of the sheath of FIG. 1 now folded to prepare it for deployment.
Figure 3:
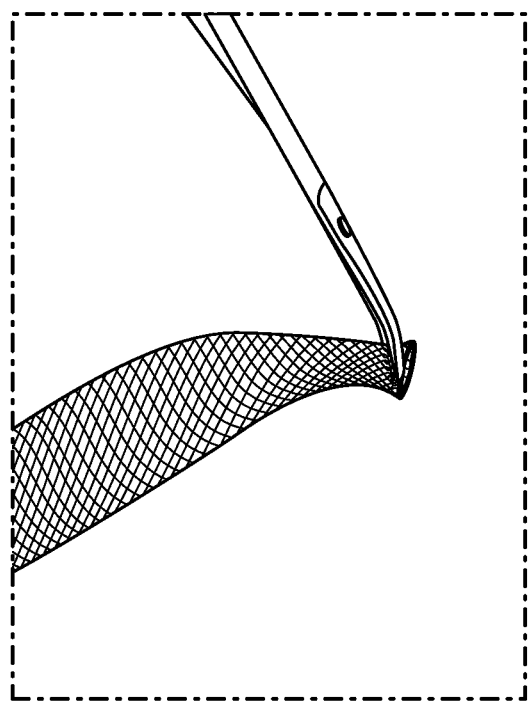
FIG. 3 is a perspective view of a deployment tool grasping the folded distal end of the sheath shown in FIG. 1 or 2.
Figure 4:
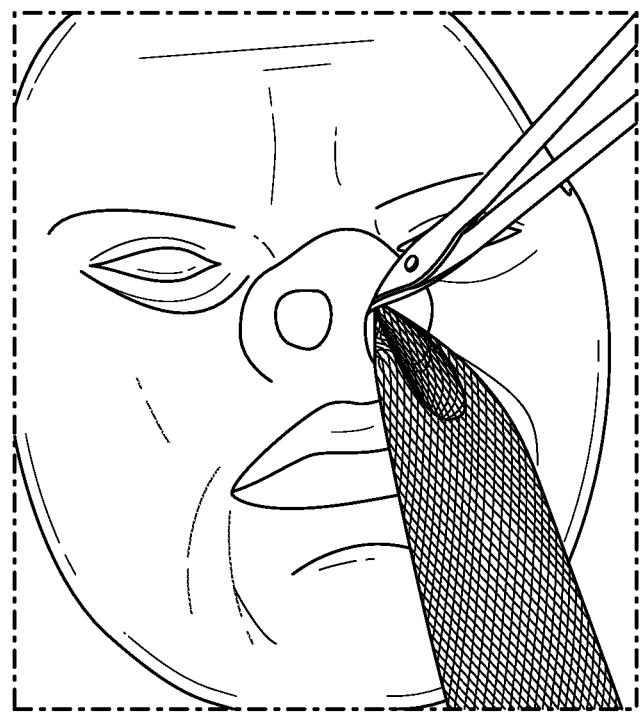
FIG. 4 is a perspective view showing the deployment tool grasping the distal end of the sheath of FIG. 1 or 2 and pulling it into the nasal cavity of the human head model.

As shown in FIG. 2, the tubular access sheath 20 may be folded to prepare it for deployment. In the example shown, the tubular shape of the sheath 20 allows any side of sheath to be folded to the opposite side. In this case the sheath 20 has no specific top/superior or bottom/inferior side. FIG. 3 shows a deployment tool 22 grasping the folded distal end of the access sheath 20. FIG. 4 shows the deployment tool 22 grasping the distal end of the access sheath 20 and pulling it into the nasal cavity. The sheath can be placed to user's preferred distal position as the length of the sheath is customizable by trimming the proximal end.

Figure 5:
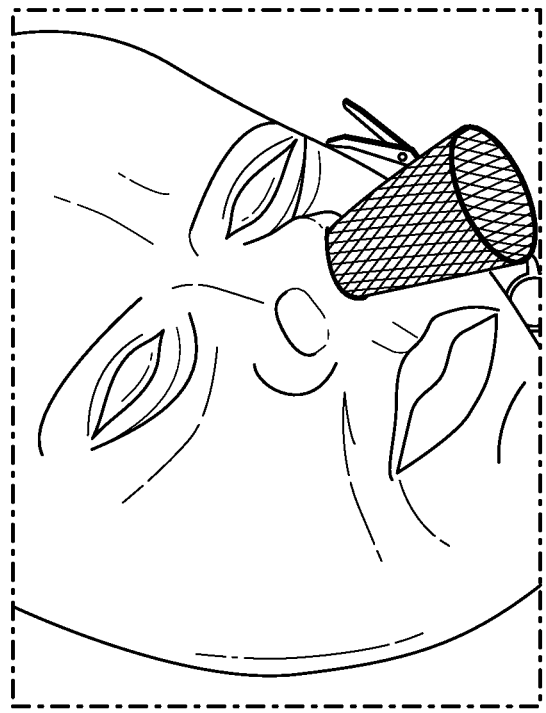
FIG. 5 is a perspective view showing the sheath of FIG. 1 or 2 now deployed and expanded in place conforming to the nasal cavity and naris of the human head model, simulating use in a human patient.
Figure 6:
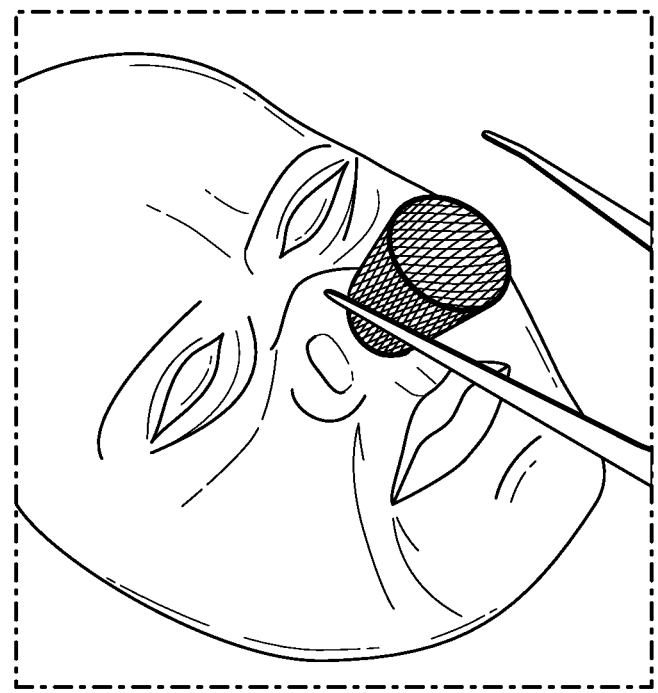
FIG. 6 is a perspective view showing the proximal end of the sheath being trimmed to a desired length using a scissor.
Figure 7:
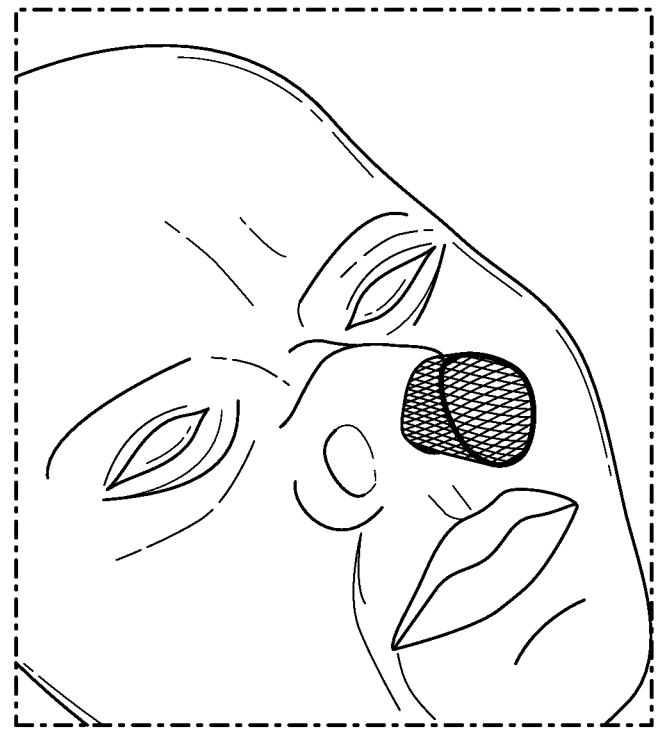
FIG. 7 is a perspective view showing the final configuration of the sheath deployed in the human head model and trimmed to the desired length.

FIG. 5 shows the sheath 20 now deployed and expanded in place conforming to the nasal cavity and naris of the patient. The naris constricts the expanded sheath 20 to hold it in place and help to minimize migration in or out of the nasal cavity. The extra length of the second or proximal end of the sheath 20 is exposed, leaving 5 to 30 mm of a second end of the sheath projecting out of the nose and ready to be cut off. FIG. 6 shows the proximal end of the sheath 20 being trimmed to a preferred length, using a cutting tool, such as a scissors. FIG. 7 shows the final configuration of sheath 20 now trimmed to the desired length. The sheath 20 may be trimmed on the proximal exposed end so that any fraying of the braid would not touch the patient.

The sheath may be designed and manufactured and described in U.S. Patent Application Publication Nos. US2017/0347865 and 2019/0104929, incorporated herein by reference.

Thus, novel sheaths and methods have been shown and described. Various changes and substitutions may of course be made without departing from the spirit and scope of the invention. The invention, therefore, should not be limited, except to the following claims and their equivalents.

The invention claimed is:
1. A surgical method, comprising:
providing a surgical sheath comprising a tube of braided material;

grasping a first end of the sheath with a distal end of a tool;
inserting the distal end of the tool into the nose of a patient;
using the tool to pull the first end of the sheath into the nose of the patient;
releasing the first end of the sheath; and
cutting off a portion of a second end of the sheath.

2. The method of claim 1 wherein 5 to 30 mm of the sheath projects out of the nose after the sheath is pulled into the nose.

3. The method of claim 1 wherein the tube has a circular cross section that is uniform along the length of the tube.

4. The method of claim 1 wherein the sheath has a constant outside diameter along its length.

5. The method of claim 1 with the sheath comprising silicone on the braided material.

6. The method of claim 1 with the sheath having a length of 70 to 180 mm.

7. The method of claim 6 with the sheath having an outside diameter of 12 to 50 mm.

8. The method of claim 1 further including using a scissor to perform the cutting.

9. The method of claim 1 further comprising folding the first end of the sheath, grasping the folded first end of the sheath with the distal end of the tool, and releasing the folded first end of the sheath after the first end of the sheath is pulled into the nose.

10. A surgical method, comprising:
providing a surgical sheath comprising a tube of braided material;
grasping a first end of the sheath with a distal end of a tool;
inserting the distal end of the tool into the nose of a patient;
using the tool to pull the first end of the sheath into the nose of the patient;
releasing the first end of the sheath, leaving a second end of the sheath projecting out of the nose; and
cutting off a portion of the second end of the sheath.

11. The method of claim 10 wherein the tube has a circular cross section that is uniform along the length of the tube.

12. The method of claim 10 wherein the sheath comprises silicone on the braided material.

13. The method of claim 10 wherein the sheath has a length of 70 to 180 mm.

14. The method of claim 10 further comprising folding the first end of the sheath, grasping the folded first end of the sheath with the distal end of the tool, and releasing the folded first end of the sheath after the first end of the sheath is pulled into the nose.

15. The surgical method of claim 10 further including leaving 5 to 30 mm of a second end of the sheath projecting out of the nose.

\* \* \* \* \*